US008486311B1

(12) United States Patent
Takiff et al.

(10) Patent No.: US 8,486,311 B1
(45) Date of Patent: Jul. 16, 2013

(54) EYEWEAR INCLUDING CATECHOL FUNCTIONALIZED BORON PYRROMETHENE DYE FOR NEUTRALIZING LASER THREAT

(75) Inventors: Larry Takiff, Arlington, MA (US); Kevin M. Bardon, Somerville, MA (US); Charles Lysogorski, Essex Junction, VT (US); Oliver Pentenrieder, Essex Junction, VT (US)

(73) Assignee: Revision Military, Ltd., Essex Junction, VT (US)

( * ) Notice: Subject to any disclaimer, the term of this patent is extended or adjusted under 35 U.S.C. 154(b) by 0 days.

(21) Appl. No.: 13/426,476

(22) Filed: Mar. 21, 2012

(51) Int. Cl.
*F21V 9/00* (2006.01)
*G02B 5/02* (2006.01)
*G02C 7/10* (2006.01)
*G02F 1/361* (2006.01)
*G03B 11/00* (2006.01)
*C07D 295/00* (2006.01)
*C07F 5/02* (2006.01)

(52) U.S. Cl.
USPC ...... 252/582; 257/40; 257/E51.024; 427/162; 544/69; 548/405

(58) Field of Classification Search
USPC 252/582; 257/40, E51.024; 427/162; 544/69; 548/405
See application file for complete search history.

(56) References Cited

U.S. PATENT DOCUMENTS

| 4,812,142 | A | 3/1989 | Brodmann |
| 6,348,596 | B1 | 2/2002 | Lee et al. |
| 2004/0221403 | A1 | 11/2004 | Pyles et al. |
| 2009/0089942 | A1 | 4/2009 | Pyles et al. |

FOREIGN PATENT DOCUMENTS

EP 1 739 119 A1 1/2007

OTHER PUBLICATIONS

Gabe et al., Highly sensitive fluorescence probes for nitric oxide based on boron dipyrromethene chromophore-rational design of potentially useful bioimaging fluorescence probe. J Am Chem Soc. Mar. 17, 2004;126(10):3357-67.
Loudet et al., BODIPY dyes and their derivatives: syntheses and spectroscopic properties. Chem Rev. Nov. 2007;107(11):4891-932. Epub Oct. 9, 2007.
Marme et al., Inter- and intramolecular fluorescence quenching of organic dyes by tryptophan. Bioconjug Chem. Nov.-Dec. 2003;14(6):1133-9.
Nierth et al., Anthracene-BODIPY dyads as fluorescent sensors for biocatalytic Diels-Alder reactions. J Am Chem Soc. Mar. 3, 2010;132(8):2646-54. doi: 10.1021/ja9084397.
Roller et al., The determination of the Förster distance (R0) for phenanthrene and anthracene derivatives in poly(methyl methacrylate) films. J Phys Chem B. Jun. 30, 2005;109(25):12261-9.
Shah et al., Pyrromethene-BF2 complexes as Laser Dyes:1. Heteroat Chem. 1990;1(5):389-99.
Sunahara et al., Design and synthesis of a library of BODIPY-based environmental polarity sensors utilizing photoinduced electron-transfer-controlled fluorescence ON/OFF switching. J Am Chem Soc. May 2, 2007;129(17):5597-604. Epub Apr. 11, 2007.

(Continued)

*Primary Examiner* — Bijan Ahvazi
(74) *Attorney, Agent, or Firm* — Wolf, Greenfield & Sacks, P.C.

(57) ABSTRACT

The embodiments described herein generally relate to compositions and articles including dye compounds having desirable optical properties, and related methods. In some cases, the compositions and articles may possess advantageous optical properties, including various degrees of absorbance, emission, and/or transmission at particular wavelengths or ranges of wavelength. Embodiments described herein may be useful as optical filters in protective eyewear applications.

18 Claims, 8 Drawing Sheets

OTHER PUBLICATIONS

Tahtaoui et al., Convenient method to access new 4,4-dialkoxy- and 4,4-diaryloxy-diaza-s-indacene dyes: Synthesis and spectroscopic evaluation. J Org Chem. Jan. 5, 2007;72(1):269-72.

Treibs et al., Difluorboryl-Komplexe von Di- und Tripyrrylmethenen. Liebigs Ann Chem. 1968;718:208-23.

Ueno et al., Mechanism-based molecular design of highly selective fluorescence probes for nitrative stress. J Am Chem Soc. Aug. 23, 2006;128(33):10640-1.

Vos De Wael et al., Pyrromethene-BF2, complexes (4,4'-difluoro-4-bora-3a,4a-diaza-s-indacenes). Synthesis and luminescence properties. Red Tray Chim Pays-Bas. 1977;96:306-9.

Ziessel et al., Boron dipyrromethene dyes: a rational avenue for sensing and light emitting devices. Dalton Trans. Jun. 21, 2006;(23):2913-8. Epub May 3, 2006.

Ziessel et al., Isocyanate-, isothiocyanate-, urea-, and thiourea-substituted boron dipyrromethene dyes as fluorescent probes. J Org Chem. Apr. 14, 2006;71(8):3093-102.

REV013

EYEWEAR INCLUDING CATECHOL FUNCTIONALIZED BORON PYRROMETHENE DYE FOR NEUTRALIZING LASER THREAT

FIELD

Compositions and articles including boron pyrromethene compounds, and related methods, are described.

BACKGROUND

Battlefield lasers are an increasing threat to warfighters. Existing eye protection typically involves the use of broad band dyes at high enough dye levels to be protective against multiple wavelengths, but often allowing too little ambient light transmission (e.g., visible light transmission) for good vision, especially at night and in low-light conditions. Visible light transmission is broken down into photopic luminous transmittance (daytime) and scotopic luminous transmittance (nighttime or low-light conditions). Scotopic luminous transmittance for eye protection incorporating 532 nm and 1064 nm blocking dyes is currently below about 10%, which essentially precludes use of these lenses at low light levels.

SUMMARY

Articles are provided comprising an optical filter including a substantially optically transparent polymer and a boron pyrromethene compound associated with the polymer, wherein the optical filter has a quantum yield of fluorescence of less than 5% upon exposure to electromagnetic radiation between about 300 nm and about 600 nm.

Articles are provided comprising an optical filter including a substantially optically transparent polymer and a boron pyrromethene compound associated with the polymer, wherein, when the article has an optical density of about 4 at an absorbance wavelength, the article has a scotopic luminous transmittance (SLT) from about 10% to about 50%.

Compositions comprising boron pyrromethene compounds are also provided. In some embodiments, the compound has the following structure, wherein:
each $R^1$-$R^6$ can be the same or different and each is hydrogen, halo, alkyl, alkenyl, alkynyl, cycloalkyl, cycloalkenyl, heterocyclyl, aryl, heteroaryl, OR', N(R')$_2$, or SR', any of which is optionally substituted; and any two of $R^1$-$R^6$ can be joined to form a ring, optionally substituted;

$R^7$ is hydrogen, halo, alkyl, alkenyl, alkynyl, cycloalkyl, cycloalkenyl, heterocyclyl, aryl, heteroaryl, OR', N(R')$_2$, or SR', any of which is optionally substituted;

each $R^8$-$R^{11}$ can be the same or different and each is hydrogen, halo, alkyl, alkenyl, alkynyl, cycloalkyl, cycloalkenyl, heterocyclyl, aryl, heteroaryl, OR', N(R')$_2$, or SR', any of which is optionally substituted; and any two of $R^8$-$R^{11}$ can be joined to form a ring, optionally substituted; and R' is hydrogen, alkyl, alkenyl, alkynyl, cycloalkyl, cycloalkenyl, heterocyclyl, aryl, or heteroaryl, any of which is optionally substituted.

Methods for forming, processing, and/or using the compositions and articles described herein are also provided.

BRIEF DESCRIPTION OF THE DRAWINGS

FIG. 1 shows (a) a boron pyrromethene structure, (b) some examples of boron pyrromethene compounds as described herein, and (c) an example of eyewear in which boron pyrromethene compounds may be incorporated.

FIG. 5 shows the absorbance and transmittance spectra for another catechol-functionalized boron pyrromethene compound (REV068) (a) in a solution of dichloromethane and (b) in a polycarbonate film.

FIG. 8 shows (a) a non-catechol-functionalized boron pyrromethene compound (REV013), and (b) log scale fluorescence spectra and (c) regular fluorescence spectra for polycarbonate plaques containing either REV013, REV063, or no boron pyrromethene compound.

FIG. 9 shows (a) log scale fluorescence emission spectra and (b) regular fluorescence emission spectra for a non-catechol-functionalized boron pyrromethene compound (REV013) in polycarbonate film, a catechol-functionalized boron pyrromethene compound (REV063) in polycarbonate film, and a polycarbonate film with no dye, when excited at 480 nm.

Other aspects, embodiments and features will become apparent from the following detailed description when considered in conjunction with the accompanying drawings. The accompanying figures are schematic and are not intended to be drawn to scale. For purposes of clarity, not every component is labeled in every figure, nor is every component of each embodiment shown where illustration is not necessary to allow those of ordinary skill in the art to understand the embodiments described herein. All patent applications and patents incorporated herein by reference are incorporated by reference in their entirety. In case of conflict, the present specification, including definitions, will control.

DETAILED DESCRIPTION

Embodiments described herein may be useful in a wide range of applications, including optical filters and applications provided with optical filters such as eyewear, namely, lenses, eyeglasses, goggles, visors, and the like. For example, articles including compounds described herein may be used as optical filters having the ability to substantially block or absorb emissions having a particular wavelength or that are within a particular wavelength range, while simultaneously allowing other emissions to be transmitted through the article. In one set of embodiments, the article may be capable of blocking or absorbing hazardous laser radiation (e.g., laser radiation at about 532 nm), while simultaneously allowing other visible light to be transmitted through the article. For example, the article may be laser protective eyewear fabricated using a boron pyrromethene compound and an optically transparent, high-strength ballistic material such as polycarbonate. Such embodiments may provide enhanced levels of visible light transmission during daytime and/or nighttime or low-light conditions, excellent protection against common laser threats, and good environmental stability and robustness.

The embodiments described herein generally relate to compositions including dye compounds having desirable optical properties, and related optical filters including such dye compounds to provide protection against light of a particular wavelength (e.g., laser light) without inhibiting vision. Embodiments described herein may possess advantageous optical properties, including various degrees of absorbance, emission, and/or transmission at particular wavelengths or ranges of wavelength. Compositions described herein may be readily synthesized and/or purified, and may exhibit sufficient photochemical and/or thermal stability to be processed, for example, via injection molding.

In some embodiments, the composition exhibits strong light absorbance at particular wavelengths, or ranges of wavelength. For example, the composition may have a strong and narrow absorbance band at a particular wavelength or wavelengths (e.g., about 532 nm), yet have relatively low absorbance at other wavelengths. Such compositions may be useful in applications where selective absorbance of light may be desired, such as optical filters, for example. In one set of embodiments, the composition may be incorporated into eyewear for protection against laser light, as described more fully below. Compositions having a narrow absorbance band may advantageously enhance the transmission of light at other wavelengths.

In one set of embodiments, the composition or article exhibits a strong, narrow absorbance band at or near about 532 nm when exposed to electromagnetic radiation. That is, the compositions may absorb light at or near 532 nm but may allow for high visible light transmission at other wavelengths.

In some embodiments, the composition or article may exhibit an enhancement of one or more components of visible light transmission, such as photopic luminous transmission (e.g., daytime transmittance) and/or scotopic luminous transmittance (e.g., nighttime transmittance). For example, eyewear articles may allow for enhanced vision at night and/or in low-light conditions. In some embodiments, articles including a dye compound as described herein may exhibit a scotopic luminous transmittance (SLT) from about 10% to about 50% when the article has an optical density of about 4 at a selected absorbance wavelength (e.g., 532 nm). In some embodiments, the article may exhibit an SLT of about 10%, about 15%, about 20%, about 25%, about 30%, about 35%, about 40%, about 45%, or about 50%, when the article has an optical density of about 4 at a selected absorbance wavelength. In one set of embodiments, articles including a dye compound as described herein may exhibit an SLT of about 30%, when the article has an optical density of about 4 at a selected absorbance wavelength. In some embodiments, articles including a dye compound as described herein may exhibit photopic luminous transmittance (PLT) of about 30%, about 40%, about 50%, or about 60%, when the article has an optical density of about 4 at a selected absorbance wavelength. In one set of embodiments, articles including a dye compound as described herein may exhibit a PLT of about 40%, when the article has an optical density of about 4 at a selected absorbance wavelength.

In some embodiments, articles including a dye compound as described herein may exhibit a PLT of about 30% and an SLT of about 10%, a PLT of about 40% and an SLT of about 10%, or a PLT of about 50% and an SLT of about 10%, when the article has an optical density of about 4 at a selected absorbance wavelength. In some embodiments, articles including a dye compound as described herein may exhibit a PLT of about 30% and an SLT of about 20%, a PLT of about 40% and an SLT of about 20%, or a PLT of about 50% and an SLT of about 20%, when the article has an optical density of about 4 at a selected absorbance wavelength. In some embodiments, articles including a dye compound as described herein may exhibit a PLT of about 30% and an SLT of about 30%, a PLT of about 40% and an SLT of about 30%, or a PLT of about 50% and an SLT of about 30%, when the article has an optical density of about 4 at a selected absorbance wavelength. In one set of embodiments, articles including a dye compound as described herein (e.g., a boron pyrromethene compound) may exhibit PLT of about 50% and an SLT of about 30%, when the article has an optical density of about 4 at a selected absorbance wavelength.

In some embodiments, the composition or article may be substantially non-fluorescent upon exposure to electromagnetic radiation, i.e., the composition or article may have a quantum yield of fluorescence of about 5% or less when exposed to electromagnetic radiation between about 300 nm and about 600 nm.

Some embodiments provide compositions including a boron pyrromethene compound. (FIG. 1A) In some embodiments, the boron pyrromethene compound may be selected to exhibit one or more of a particular, desired optical property (e.g., absorbance, fluorescence, phosphorescence, chemiluminescence, etc.) upon exposure to electromagnetic radiation. For example, the composition may exhibit a narrow absorbance peak at a particular wavelength, allowing the composition to serve as an optical filter as it absorbs a specific wavelength of light (e.g., harmful laser light) while allowing other light to pass through the composition. In some cases, the boron pyrromethene compound may be appropriately substituted to exhibit a maximum absorbance peak at a particular wavelength upon exposure to electromagnetic radiation. The selection of different substituents on the boron pyrromethene compound may shift the wavelength at which the composition exhibits a maximum absorbance peak, producing optical filters that can absorb/filter light of different wavelengths.

For example, to filter light having relatively shorter wavelengths, the compound may be substituted with one or more electron-poor groups, such as acyl, carboxyl, cyano, nitro, sulfonate, fluoroalkyls, or the like, such that a maximum absorbance peak of the compound is shifted to relatively shorter wavelengths (e.g., blue-shifted). In cases where it is desirable to filter light having relatively longer wavelengths, the compound may be substituted with one or more electron-rich groups, such as amino, hydroxy, alkoxy, acylamino, acyloxy, alkyl, halide, and the like, such that a maximum absorbance peak of the compound is shifted to relatively longer wavelengths (e.g., red-shifted). In some cases, the boron pyrromethene compound may be substituted with a combination of electron-poor and electron-rich groups. The maximum absorbance peak may be a particular peak having the largest intensity in an absorbance spectrum, or, alternatively, the maximum absorbance peak may be a peak in an absorbance spectrum that has at least a defined maximum, but has a smaller intensity relative to other peaks in the absorbance spectrum.

In some embodiments, the boron pyrromethene compound has a maximum absorbance peak between about 400 and about 800 nm. In some embodiments, the boron pyrromethene compound has a maximum absorbance peak, between about 470 and about 800 nm, between about 500 and about 800 nm, or between about 500 and about 650 nm. In some cases, the boron pyrromethene compound has a maximum absorbance peak of about 400, about 425, about 450, about 475, about 500, about 525, about 550, about 575, about 600, about 625, about 650, about 675, about 700, about 725, about 750, about 775, or about 800 nm. In some embodiments, the boron pyrromethene compound has a maximum absorbance peak within about 15 nm, within about 10 nm, within about 5 nm, or within about 2 nm of a particular desired wavelength, as described herein. In some embodiments, the boron pyrromethene compound has a maximum absorbance peak of about 532 nm. In some embodiments, the boron pyrromethene compound has a maximum absorbance peak of about 455 nm.

Some embodiments may involve the use of boron pyrromethene compounds that can selectively filter a specific, narrow band of light while allowing other light to be transmitted so as to not interfere with normal vision. Such compounds may exhibit a relatively narrow absorbance peak. For example, the compound may exhibit a strong absorbance peak at a particular wavelength in the visible spectrum, while minimizing absorbance of light at other wavelengths and maximizing transmission of visible light. Such compounds may be useful, for example, as optical filters.

In some embodiments, optical properties which would interfere with normal vision (e.g., fluorescence emission, light scattering) may be reduced or eliminated. In some cases, the boron pyrromethene compound may be selected to exhibit a relatively low, or substantially no, fluorescence emission upon exposure to electromagnetic radiation in order to improve vision through the optical filter. In some cases, the composition or article has a quantum yield of fluorescence of about 5% or less upon exposure to electromagnetic radiation between about 300 nm and about 600 nm. In some cases, the composition or article has a quantum yield of fluorescence of about 0.01% to about 5%, about 0.01% to about 4%, about 0.01% to about 3%, about 0.01% to about 2%, or about 0.01% to about 1%, upon exposure to electromagnetic radiation between about 300 nm and about 600 nm.

In some cases, a solid article containing a boron pyrromethene compound as described herein may exhibit low or substantially no fluorescence emission upon exposure to electromagnetic radiation. In some cases, a solution containing a boron pyrromethene compound as described herein may exhibit low or substantially no fluorescence emission upon exposure to electromagnetic radiation. In some embodiments, the boron pyrromethene compound may be highly fluorescent in both solution (e.g., a chloroform solution) and in solid form (e.g., in a polycarbonate matrix). In some embodiments, the boron pyrromethene compound may be highly fluorescent in solution but may be substantially non-fluorescent in solid form. In other embodiments, the boron pyrromethene compound may be highly fluorescent in solid form but may be substantially non-fluorescent in solution. The quantum yield of fluorescence, or fluorescence yield, of a material refers to the ratio of photons emitted through fluorescence to photons absorbed. Those of ordinary skill in the art would be able to select a method for measuring the quantum yield of fluorescence of a material, including comparison of the fluorescence emission of a known standard dye compound with that of a test dye compound. Typically, samples which absorb an essentially identical number of photons are compared, e.g., by comparing samples having essentially identical optical densities at a particular wavelength when exposed to an essentially identical set of conditions (e.g., electromagnetic radiation having the same wavelength) or by adjusting the fluorescence emission data to correct for any differences in absorbance value and/or concentration between the standard and the test samples. For example, the fluorescence emission intensity of a test dye in film may be adjusted to account for any differences in absorbance value and concentration when compared to the reported fluorescence emission intensity of known standard dye. The quantum yield of fluorescence of the test dye in film may then be calculated based on the difference between fluorescence emission intensities of the standard dye and test dye in film, as well as the reported quantum yield of fluorescence for the standard dye in film.

Without wishing to be bound by any theory, reduced fluorescence in some boron pyrromethene compounds may be attributed to an intramolecular electron transfer reaction, i.e., electron transfer from one portion of the molecule to another portion of the molecule, that quenches fluorescence. For example, the compound may include one portion including electron-rich groups and another portion including electron-poor groups, creating a molecular dipole moment and resulting in a reduced fluorescence, or substantially no fluorescence, upon exposure to electromagnetic radiation.

In some embodiments, the boron pyrromethene compound may be appropriately functionalized to impart other desired characteristics (e.g., surface properties) to the compound. For example, the boron pyrromethene compound may include substituents that can alter or improve properties such as compatibility with a medium (e.g., solubility, stability), photostability, and/or thermal stability. In some cases, the boron pyrromethene compound may comprise functional groups selected to possess an affinity for a surface. In some embodiments, the polymer comprises a sterically bulky group that may aid in preserving the optical properties of the compound, even in the solid state. Some embodiments may involve boron pyrromethene compounds substituted with various alkyl groups, for example, to enhance solubility or compatibility of the compound in a hydrophobic medium and/or to tailor the maximum absorbance peak of the compound.

Figure 1A:
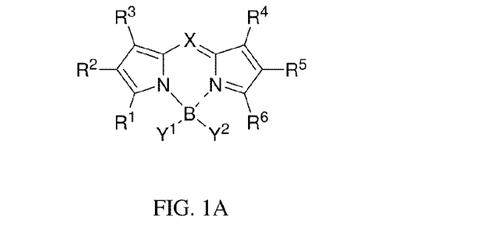

The boron pyrromethene compound may have a structure as shown in FIG. 1A, wherein:

each $R^1$-$R^6$ can be the same or different and each is hydrogen, halo, alkyl, alkenyl, alkynyl, cycloalkyl, cycloalkenyl, heterocyclyl, aryl, heteroaryl, OR', N(R')$_2$, or SR', any of which is optionally substituted; and any two of $R^1$-$R^6$ can be joined to form a ring, optionally substituted;

X is N or $CR^7$, wherein $R^7$ is hydrogen, halo, alkyl, alkenyl, alkynyl, cycloalkyl, cycloalkenyl, heterocyclyl, aryl, heteroaryl, OR', N(R')$_2$, or SR', any of which is optionally substituted;

$Y^1$ and $Y^2$ can be the same or different and each is halo, OR', N(R')$_2$, or SR', any of which is optionally substituted; or $Y^1$ and $Y^2$ are joined to form a ring, optionally substituted; and R' is hydrogen, alkyl, alkenyl, alkynyl, cycloalkyl, cycloalkenyl, heterocyclyl, aryl, or heteroaryl, any of which is optionally substituted.

In some embodiments, $R^1$, $R^2$, $R^3$, $R^4$, $R^5$, and $R^6$ are each independently alkyl; X is $CR^7$; and $Y^1$ and $Y^2$ are each $OR'$, $N(R')_2$, or $SR'$, any of which is optionally substituted; or $Y^1$ and $Y^2$ are joined to form a ring, optionally substituted. In some embodiments, $Y^1$ and $Y^2$ are joined to form a ring, optionally substituted. In one set of embodiments, $Y^1$ and $Y^2$ are joined to form a catechol group or a bisnaphthol group, any of which is optionally substituted.

In one set of embodiments, the boron pyrromethene compound may comprise an electron-rich or electron donating group such as a catechol group. For example, the compound may have the following formula:

wherein:

each $R^8$-$R^{11}$ can be the same or different and each is hydrogen, halo, alkyl, alkenyl, alkynyl, cycloalkyl, cycloalkenyl, heterocyclyl, aryl, heteroaryl, $OR'$, $N(R')_2$, or $SR'$, any of which is optionally substituted; and any two of $R^8$-$R^{11}$ can be joined to form a ring, optionally substituted.

In some cases, $R^1$, $R^2$, $R^3$, $R^4$, $R^5$, and $R^6$ are each independently alkyl. In some cases, $R^1$, $R^2$, $R^3$, $R^4$, $R^5$, and $R^6$ are each independently methyl, ethyl, or propyl.

In some embodiments, $R^7$ is an optionally substituted aryl. For example, $R^7$ may be an aryl group substituted with 1-5 substituents selected from the group consisting of alkyl, aryl, $OR'$, $N(R')_2$, or $SR'$, any of which is optionally substituted, wherein R' is hydrogen, alkyl, or aryl, any of which is optionally substituted.

Examples of boron pyrromethene compounds include, but are not limited to, -continued In some cases, the article includes a boron pyrromethene compound in combination with one or more additional components. For example, the article may include a boron pyrromethene compound associated with a polymer material (e.g., polycarbonate). In some embodiments, the boron pyrromethene compound may be dispersed on or within at least a portion of the polymer. In some cases, the compound is formed as a coating on the polymer.

Some embodiments may provide an article including an optical filter including a substantially optically transparent polymer, and a boron pyrromethene compound associated with the polymer. In one particular embodiment, the article comprises polycarbonate and a boron pyrromethene compound dispersed on and/or throughout the polycarbonate. The optical filter may be a film or coating applied to the article, such as eyewear, or at least a portion of the article may be formed of the optical filter. Representative of the latter arrangement is molding an eyeglass or goggle lens from a polymer and a boron pyrromethene compound associated with the polymer.

In one set of embodiments, the article may comprise a polycarbonate and a boron pyrromethene compound including a catechol group associated with the polycarbonate, and may exhibit a combination of high absorbance at or near 532 nm, high visible light transmission, high thermal stability, and low fluorescence.

It should be understood that boron pyrromethene compounds are described by way of example only, and other, similar compounds may be useful in the context of the embodiments described herein. For example, boron azapyrromethene compounds, porphyrin compounds, boron furanopyrrole compounds (e.g., Keio dyes), and the like may also be used.

Some embodiments may involve the use of a combination of various dye compounds, each compound having an absorbance at a different wavelength. For example, the article or composition may include a mixture of different boron pyrromethene compounds, each compound having a different chemical structures and an absorbance at a different wavelength. In another example, the article or composition may include a mixture of different dye compounds, including boron pyrromethene compounds and other compounds, where each compound exhibits an absorbance at a different wavelength. Such embodiments may be used to tailor the optical properties of the composition or article, allowing for selective absorption at various wavelengths.

Various polymers may be suitable for use in the methods described herein. In some embodiments, the polymer may be an optical plastic such as polycarbonate. Other examples include, but are not limited to, polyethylene, polypropylene, poly(vinyl chloride), poly(methyl methacrylate), poly(vinyl benzoate), poly(vinyl acetate), polystyrene, cellulose, poly (vinyl pyrrolidinone), polyamide, polyacrylamide, epoxys, silicones, poly(vinyl butyral), polyurethane, nylons, polyacetal, polycarbonate, polyesters, polyethers, cyclic olefin polymers, copolymers such as polyester-polycarbonate, acrylonitrile-butadiene-styrene (ABS), crosslinked polymers such as polystyrene-poly(divinyl benzene), polyacrylamide-poly (methylenebisacrylamide), polybutadiene copolymers, combinations thereof, and the like.

Boron pyrromethene compounds may be synthesized using various methods known to those of skill in the art. Generally, a pyrrole species and an aldehyde species may react via a condensation reaction (e.g., an acid-catalyzed condensation reaction) to form a pyrromethene ligand, which may be then be reacted with a boron-containing species to form the boron pyrromethene compound. Various pyrrole species, aldehyde species, and a boron-containing species containing a range of substituents are readily accessible and known to those of skill in the art. Further modification of the boron pyrromethene compound may be carried out using known methods, including substitution of ligands attached to the boron atom and/or modification of functional groups on the pyrromethene ligand.

The compositions and articles described herein may be produced using various methods known in the art. For example, the boron pyrromethene compound may be combined with a solvent (e.g., an oil), and may then be add to a polymer (e.g., in pellet form, in powder form, etc.). The mixture may be shaken and/or stirred for a period of time to substantially uniformly associate the boron pyrromethene onto, within, and/or throughout the polymer. The concentration of boron pyrromethene in the solvent may be varied to suit a particular application. In some embodiments, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg of boron pyrromethene compound per 0.5 mL solvent may be used. Additionally, the ratio, by weight, of boron pyrromethene compound to polymer may also be varied to suit a particular application. In some embodiments, the ratio of boron pyrromethene compound to polymer may be about 1:1, about 1:2, about 1:3, about 1:4, about 1:5, about 1:10, about 1:20, about 1:30, about 1:40, about 1:50, or less, by weight. In one set of embodiments, the ratio of dye compound to polymer is about 1:5, by weight. Those of ordinary skill would be able to select the appropriate amounts of dye compound, solvent, and polymer suitable for use in a particular application.

In an illustrative embodiment, the method may be carried out using about 25 mg of boron pyrromethene compound and 100 g polycarbonate pellet in 0.5 mL of solvent. In some cases, the solvent is an oil such as bis(2-ethylhexyl)adipate (BEHA).

Boron pyrromethene compounds may also be coated onto a solid substrate by methods known to those skilled in the art, such as dip coating, rod coating, slot coating, blade coating, spin coating, and the like. For example, the compound may be combined with a solvent, and the resulting solution may be used to coat a solid substrate (e.g., a polymer substrate). Removal of the solvent (e.g., by evaporation or drying) may then produce the coated article.

The resulting material may be further processed to form articles, including molded articles. In some cases, the material may be processed using extrusion processing methods or thermoforming methods known to those skilled in this art. In some cases, the material may be processed via injection molding. In some cases, the material may be processed via thermoforming. In one set of embodiments, the polymer-boron pyrromethene material may be introduced into an extruder wherein the mixture is melted and homogenized in the barrel of the molding machine. The molten material may then be extruded either through an extrusion die or into a mold to form the finished product.

In the compounds and compositions described herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The terms "alkenyl" and "alkynyl" refer to unsaturated aliphatic groups analogous in length and possible substitution to the alkyls described above, but that contain at least one double or triple bond respectively.

As used herein, the term "halo" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The terms "heteroaryl" refers to aryl groups including at least one heteroatom as a ring atom. Suitable heteroatoms include oxygen, sulfur, nitrogen, phosphorus, and the like. Heteroaryls include, for example, thiophene, benzothiophene, thianthrene, furan, tetrahydrofuran, pyran, isobenzofuran, chromene, xanthene, phenoxathiin, pyrrole, pyrrolidine, imidazole, pyrazole, pyrazine, isothiazole, isoxazole, pyridine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, and the like. The heteroaryl ring can be optionally substituted at one or more positions with such substituents as described herein. In some cases, the heteroaryl may be bonded to a compound via a heteroatom ring atom (e.g., nitrogen). In some cases, the heteroaryl may be bonded to a compound via a carbon ring atom.

The terms "amine" and "amino" are art-recognized and refer to both unsubstituted and substituted amines, e.g., a moiety that can be represented by the general formula: N(R') (R")(R"') wherein R', R", and R"' each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that a "substituted" compound is a stable compound, e.g., one which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the embodiments described herein, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

EXAMPLES

Example 1

The following example describes a general synthetic procedure for catechol-derivatized dyes. To generate the dipyrromethane ligand, a solution of pyrrole (2 eq) and aldehyde (1 eq) were dissolved in anhydrous dichloromethane under an Ar atmosphere. One drop of trifluoroacetic acid (TFA) was added and the solution was stirred at room temperature overnight. Upon complete consumption of the aldehyde, 2,3- dichloro-5,6-dicyano-1,4-benzoquinone (DDQ) (1 eq) was added and stirring was continued for 15 min. The reaction mixture was washed several times with water, the organic portion was recovered, dried over $Na_2SO_4$, filtered and carried on to the next step without further purification.

The dipyrromethene solution in dichloromethane was thoroughly sparged with Ar whilst stirring, then diisopropylethylamine (10 eq) was added. The reaction mixture was sparged whilst stirring for an additional 20 min, at which point it was carefully treated with boron trifluoride diethyl etherate solution ($BF_3.OEt_2$) (14 eq) under inert atmosphere and allowed to stir vigorously as such at room temperature overnight. Upon completion, the reaction mixture was stirred with an equal volume of water for 30 min, then the organic portion was washed several times more, collected, dried over $Na_2SO_4$, filtered and adsorbed onto silica powder. The material was then subjected to flash column chromatography (FCC) using a hexane/ethyl acetate gradient to elute the difluoro-BODIPY dye.

The difluoro-BODIPY dye (1 eq) was then dissolved in anhydrous dichloromethane in the presence of aluminum chloride ($AlCl_3$) (1.5 eq) under Ar. The resulting mixture was refluxed for 5 min prior to the addition of catechol (4 eq). After 5 min at room temperature, the crude mixture was concentrated under reduced pressure, adsorbed onto deactivated basic alumina and purified by FCC on a deactivated basic alumina column using a hexane/$CH_2Cl_2$ gradient to elute the final compound.

Example 2

The following example describes a general method for preparation of films containing the boron pyrromethene dyes, as described herein. A stock solution of polycarbonate dissolved in chloroform (10% m/m) was made. The dry boron pyrromethene material was dissolved in a small volume of the 10% polycarbonate/chloroform solution (5-10 mg/mL), homogenized, and then distributed onto a polyester film substrate. The dye solution was immediately pulled unidirectionally at a steady, moderate rate using a #18 wire-wound rod (RD Specialties, NY) to produce a uniform film coating. Upon drying, spectral characterization and analysis was conducted.

Figure 2:
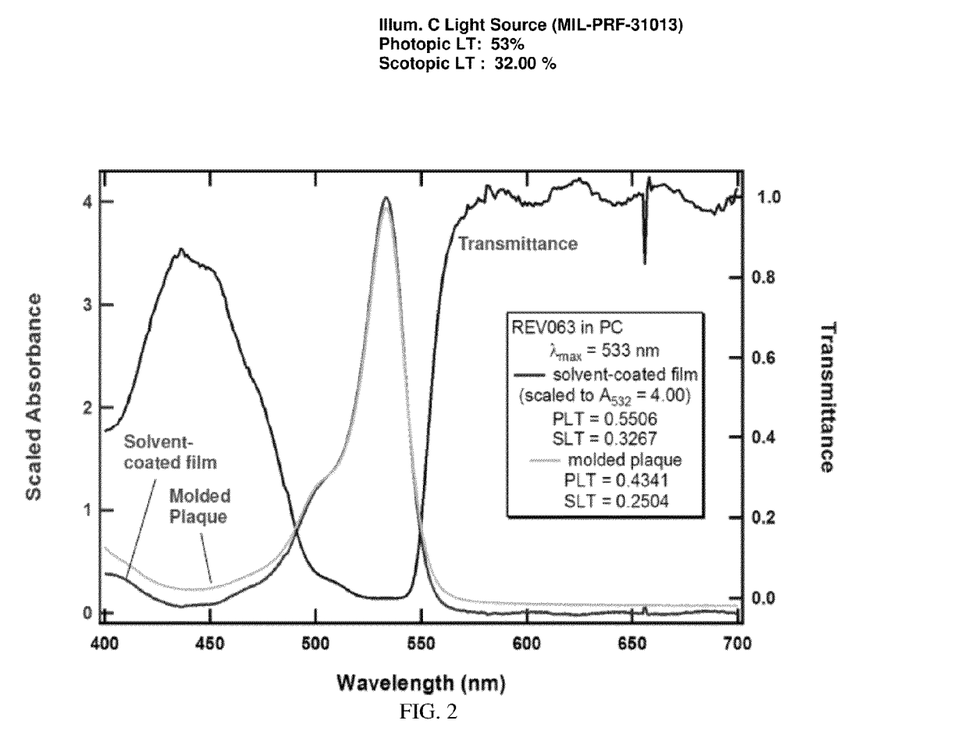
FIG. 2 shows the absorbance and transmittance spectra for a catechol-functionalized boron pyrromethene compound (REV063) in a polycarbonate film and a molded plaque of polycarbonate.
Figure 3:
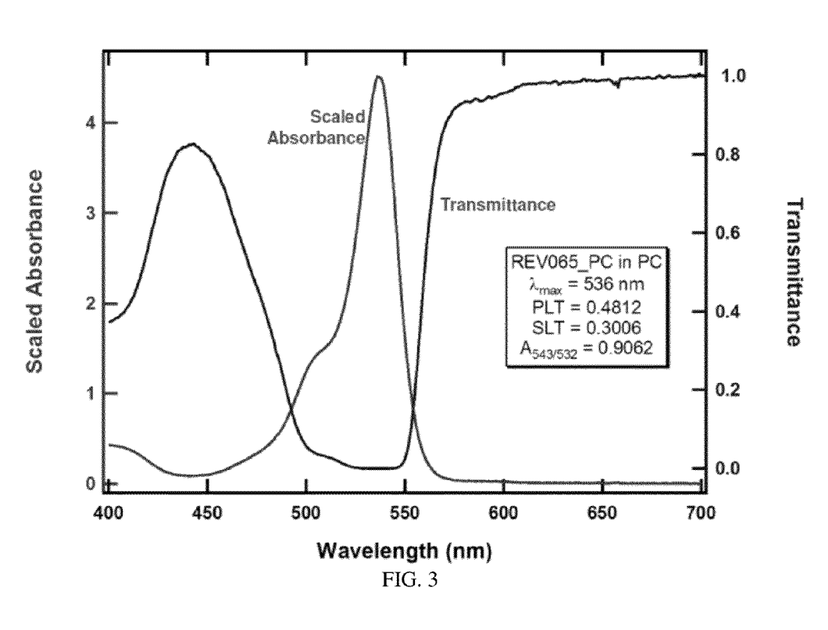
FIG. 3 shows the absorbance and transmittance spectra for another catechol-functionalized boron pyrromethene compound (REV065) in a polycarbonate film.
Figure 4:
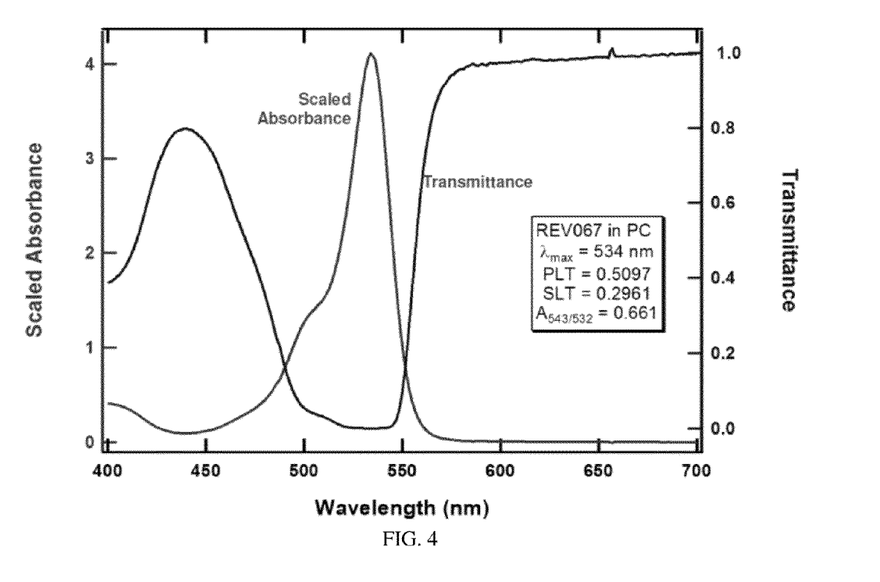
FIG. 4 shows the absorbance and transmittance spectra for another catechol-functionalized boron pyrromethene compound (REV067) in a polycarbonate film.
Figure 5A:
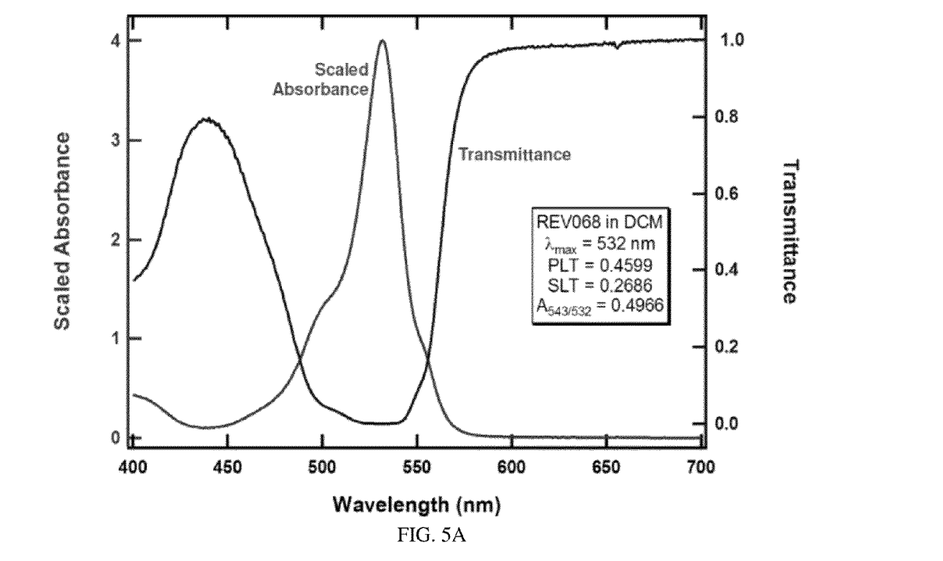
Figure 5B:
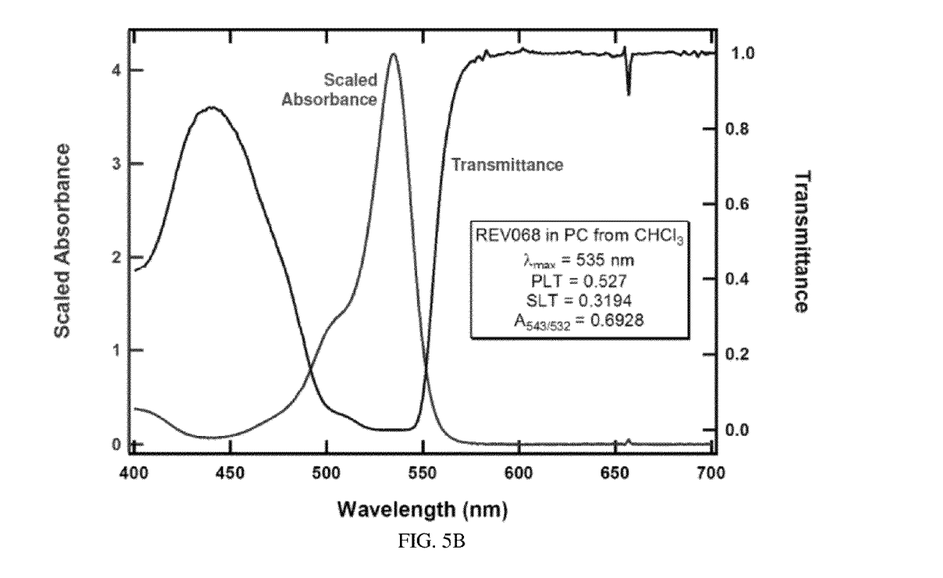
Figure 6:
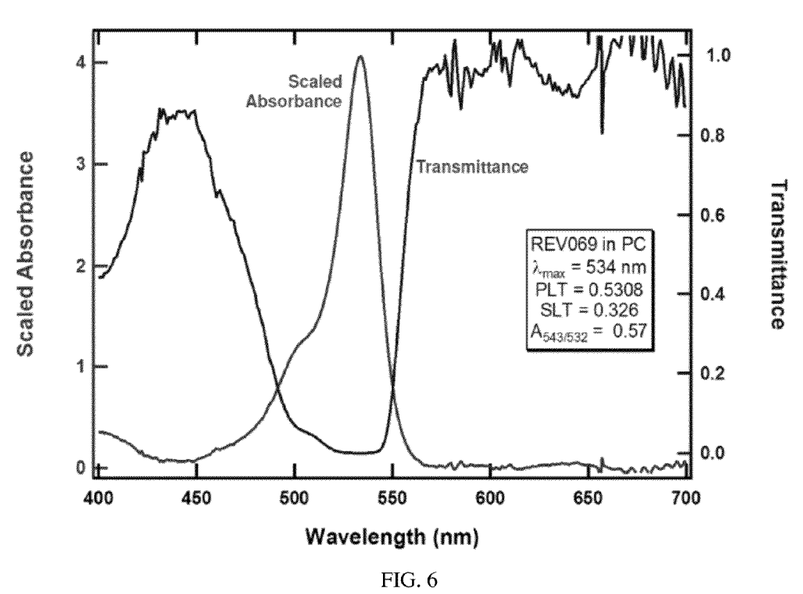
FIG. 6 shows the absorbance and transmittance spectra for another catechol-functionalized boron pyrromethene compound (REV069) in a polycarbonate film.

FIG. 2 shows the absorbance and transmittance spectra for a catechol-functionalized boron pyrromethene compound (REV063) in a polycarbonate film and a molded plaque of polycarbonate (50 mm square, 2.2 mm thickness). The film containing REV063 exhibited an SLT of about 33% and the molded plaque exhibited an SLT of about 25%. FIG. 3 shows the absorbance and transmittance spectra for another catechol-functionalized boron pyrromethene compound, REV065, in a polycarbonate film. The film containing REV065 exhibited similar performance as REV063, with an SLT of about 30%. FIG. 4 shows the absorbance and transmittance spectra for another catechol-functionalized boron pyrromethene compound, REV067, in a polycarbonate film, with an SLT of about 30%. FIG. 5 shows the absorbance and transmittance spectra for another catechol-functionalized boron pyrromethene compound, REV068, (a) in a solution of dichloromethane (SLT value of about 27%) and (b) in a polycarbonate film (SLT value of about 32%). FIG. 6 shows the absorbance and transmittance spectra for another catechol-functionalized boron pyrromethene compound (REV069) in a polycarbonate film, exhibiting an SLT value of about 33%.

Figure 7:
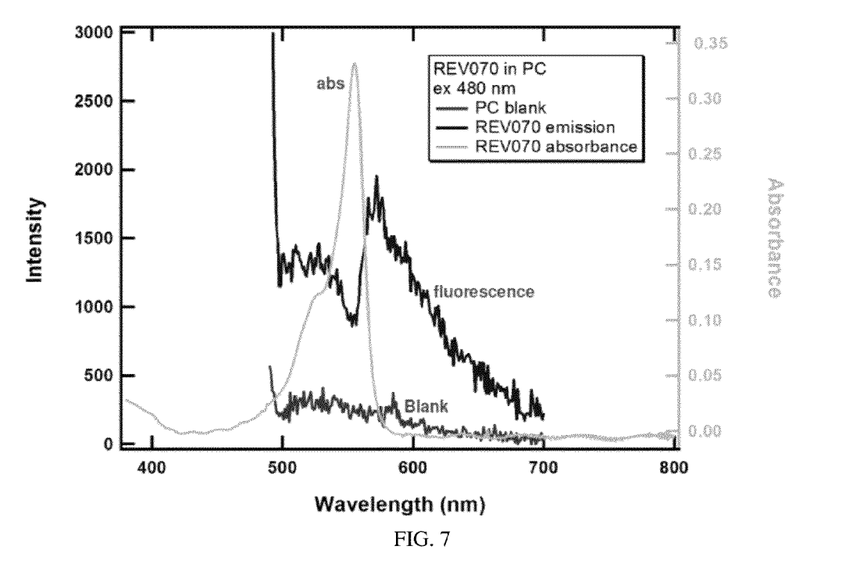
FIG. 7 shows the absorbance and fluorescence emission spectra for a catechol-functionalized boron pyrromethene compound (REV070) in a polycarbonate film, compared to that of a polycarbonate film lacking the compound.

FIG. 7 shows the absorbance and fluorescence emission spectra for a catechol-functionalized boron pyrromethene compound REV070 in a polycarbonate film, compared to that of a polycarbonate film lacking the compound. It was shown that the REV070-containing film exhibited low fluorescence at 550 nm.

Figure 8A:
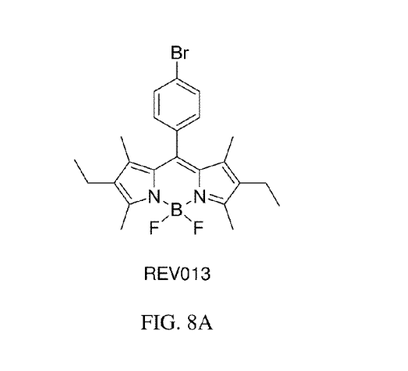
Figure 8B:
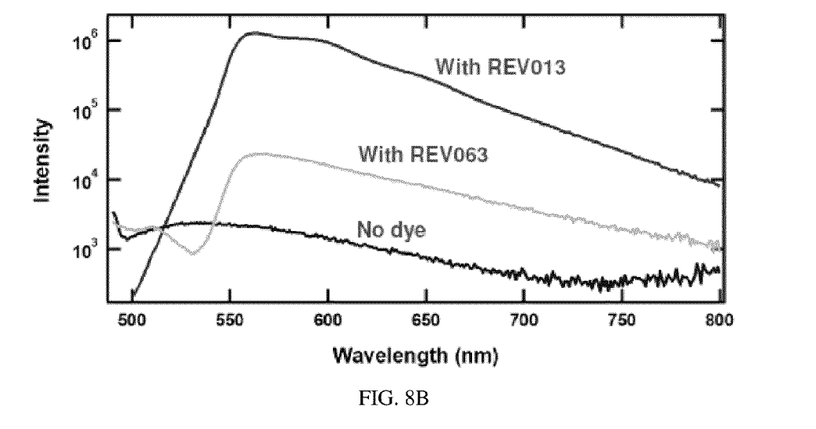
Figure 8C:
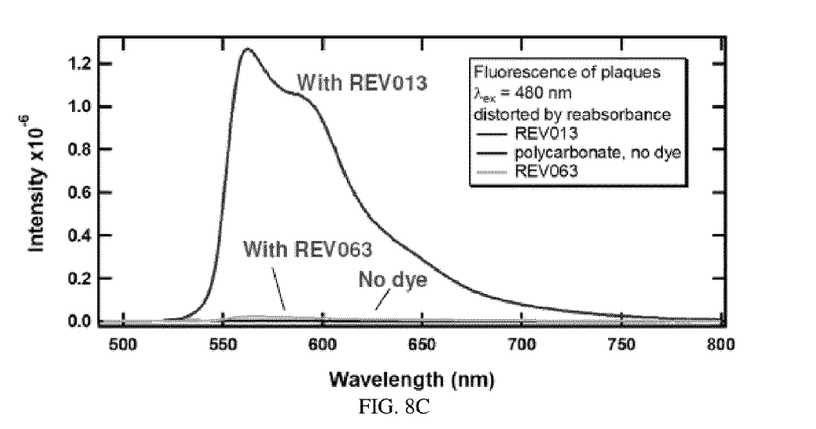

FIGS. 8B-C show fluorescence spectra for polycarbonate plaques containing either a non-catechol functionalized boron pyrromethene compound (REV013, as shown in FIG. 8A), REV063, or no boron pyrromethene compound. The fluorescence of REV063-containing film was shown to be about 55 times less than that of the REV013-containing film.

Fluorescence quantum yields for the dye-containing films were estimated by comparing reported quantum yield of fluorescence for reference dye-containing films (see Prieto, J. B. et al., J. of Luminescence 2007, 126, 833-837, for representative dye-film data) with spectral measurements for the dye-containing films described herein. By correlating UV-vis absorbances with the fluorescence emission intensities of the various films, approximate fluorescence quantum yields for the dye-containing films were calculated. The fluorescence quantum yield for previous boron pyrromethene dyes in polymer film has been reported to be in the range of about 25% to about 75%, depending on particular dye, polymer matrix, and concentrations used, with the majority falling within a range of 30-60%.

Figure 9A:
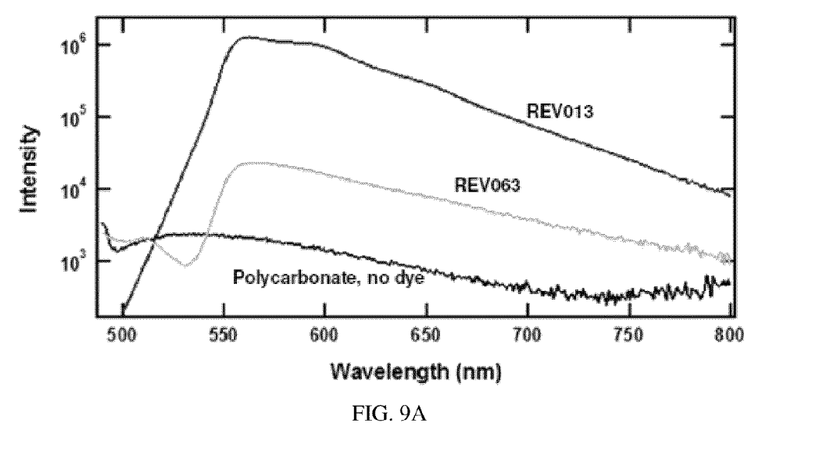
Figure 9B:
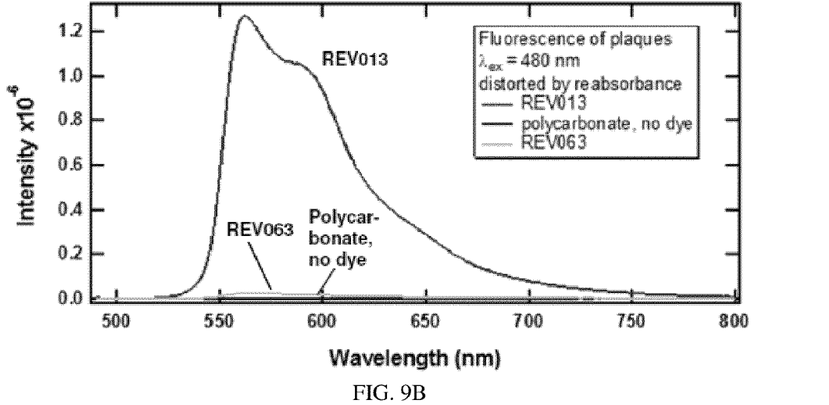

In this example, the fluorescence emission intensity of a non-catechol-functionalized boron pyrromethene compound (REV013) in polycarbonate film was compared to the fluorescence emission intensity of the catechol-functionalized boron pyrromethene compounds in polycarbonate film, correcting for absorbance values and concentrations. FIG. 9 shows representative fluorescence emission spectra for REV013 in polycarbonate film, a catechol-functionalized boron pyrromethene compound (REV063) in polycarbonate film, and a polycarbonate film with no dye, when excited at 480 nm. Compared to REV013, the boron pyrromethene dyes including a catechol group exhibited negligible fluorescence emission (i.e., nearly identical to a polycarbonate blank). Thus, the fluorescence quantum yields of these dyes were estimated to fall in a range of 0% to 1%.

Example 3

When combining dyes, a chemical interaction can take place between the dyes causing the optical density (OD) at either or both bands to change. The following example describes pulse laser testing of boron pyrromethene compounds to investigate two different narrow band dyes with peak absorption near 532 nm and their effects on OD when combined with a 1064 nm dye. Current dyes have a great reduction in OD when combined, especially post solarization of the materials. The goal of this study was to compare the change in OD of the two different dyes when combined with the currently used 1064 nm dye pre and post solarization.

Figure 1B:
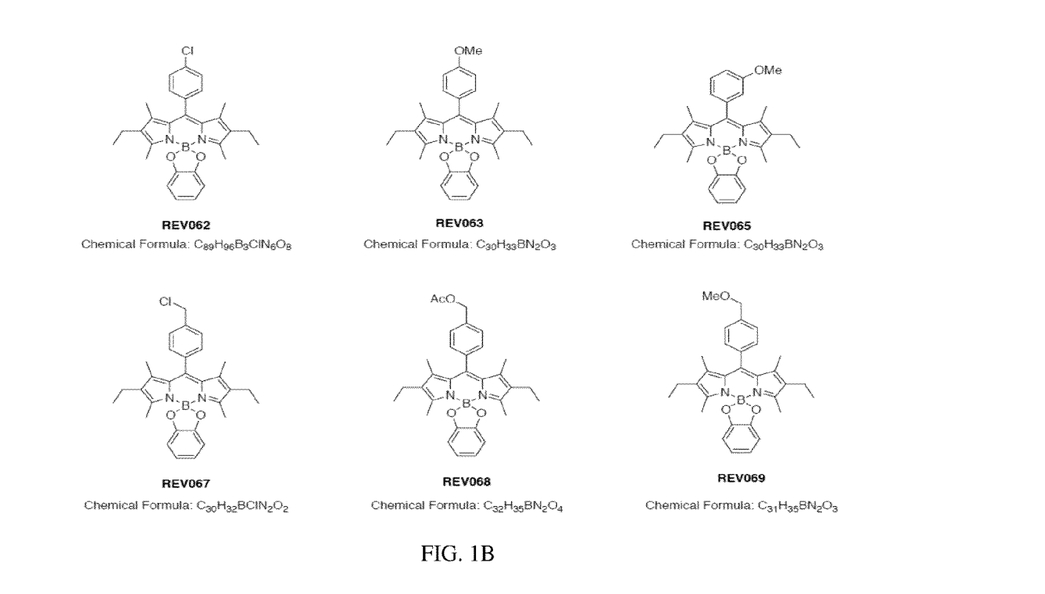
Figure 1C:
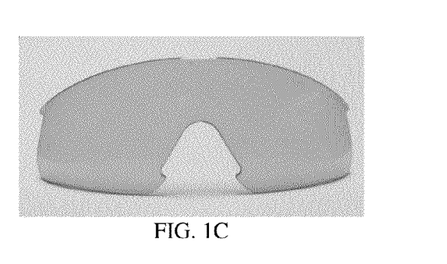

A narrow band dye with peak absorption at 527 nm (purchased from Exciton and referred to as "Exciton 527") and a narrow band boron pyrromethene dye with peak absorption at 533 nm ("REV063" as shown in FIG. 1B) were each combined in their dry fine powder state with the currently used Exciton dye to cover 1064 nm and having peak absorption at 980 nm (purchased from Exciton and referred to as "Exciton 1064"). The dry powder was dispersed in a carrier medium and used to coat optically clear polycarbonate resin. The dye coated resin was molded into 50 mm square plaques (2.2 mm thickness) and their optical properties were measured using a UV/VIS/NIR spectrophotometer as well as pulse laser testing for optical density. The sample plaques were put through a solarization procedure in order to analyze solar effects on the dyes, and pre and post solar optical data was obtained. As shown in Table 1, dye interaction with solarization and pulse mode saturation showed that a higher OD and usable light transmission was achieved with REV063.

TABLE 1

Dye interaction with solarization and pulse saturation effects.

| Sample Description | 532 OD (spectro) | % OD Change | 1064 OD (spectro) | % OD Change | Pulse 532 OD | % OD Change | Pulse 1064 OD | % OD Change |
|---|---|---|---|---|---|---|---|---|
| REV063 + 1064 | 3.92 | | 4.59 | | 3.48 | | 4.03 | −2.48 |
| REV063 + 1064 solarized | 3.61 | −7.83 | 4.05 | −11.71 | 3.54 | 1.72 | 3.93 | |
| Exciton + 1064 | 4.71 | | 5.30 | | 4.23 | | 5.20 | −20.77 |
| Exciton + 1064 solarized | 4.68 | −0.51 | 4.15 | −21.63 | 4.29 | 1.42 | 4.12 | |

| Transmission % | pre pho | pre sco | post pho | post sco |
|---|---|---|---|---|
| REV063 | 43 | 25 | 45 | 28 |
| Exciton | 36 | 18 | 34 | 16 |
| REV063 + 1064 | 37 | 11 | 31 | 11 |
| Exciton + 1064 | 27 | 8 | 18 | 7 |

Table 2 shows the optical density values measured with a spectrophotometer. Spectrophotometric VLT values for Photopic and Scotopic transmission are also presented for each sample. Lowering OD increases the VLT compared to current broad band dye formulation. While many current 532 nm lens exhibit a haze >0.6, a molded 50 mm square plaque (2.2 mm thickness) containing REV063 exhibited a haze <0.3.

TABLE 2

Optical density values for various dye compounds.

| | | | Photopic | Scotopic |
|---|---|---|---|---|
| Current 532 FT2 | 532 | OD4.0+ | 42%+ | 6%+ |
| Current 532 FT2 | 532 | OD2.1+ | 47%+ | 8%+ |
| REV063* | 532 | 4.0+ | 43%+ | 24%+ |
| REV063* | 532 | 2.1+ | 50%+ | 36%+ |

*experimental dye

In spectrophotometric measurements, it was observed that the Exciton 1064 nm dye molded into a 50 mm square polycarbonate plaque (2.2 mm thickness) had a significant drop in OD post solarization. When the Exciton 1064 dye was combined with the Exciton 527 dye in a molded, 50 mm square polycarbonate plaque (2.2 mm thickness), the OD drop at 1064 nm was even greater than for the Exciton 1064 dye alone. When the Exciton 1064 nm dye was combined with the boron pyrromethene dye REV063 in a molded, 50 mm square polycarbonate plaque (2.2 mm thickness), the OD drop at 1064 nm was significantly smaller than when molded alone. This suggested that REV063 stabilized the Exciton 1064 nm dye. However, with REV063 the absorption at 532 nm was observed to drop post solarization while with the Exciton 527 dye the absorption did not drop.

In laser pulse OD measurements, it was observed that the Exciton 1064 nm dye molded into a 50 mm square polycarbonate plaque (2.2 mm thickness) had an even greater drop in OD post solarization compared to the spectrophotometric measurement. Combination of the Exciton 527 dye with the Exciton 1064 dye in a molded, 50 mm square polycarbonate plaque (2.2 mm thickness) also showed a large decrease in OD at 1064 nm, though less than the plaque containing the 1064 nm dye. The combination of the boron pyrromethene dye REV063 with the Exciton 1064 dye in a molded, 50 mm square polycarbonate plaque (2.2 mm thickness) showed a relatively small decrease in OD at 1064 nm post solarization, indicating still that the that the boron pyrromethene dye stabilized the system greatly.

Visible light transmission (VLT) values were also acquired showing a much higher photopic and higher scotopic transmission using the boron pyrromethene dye compared to the Exciton dye. Although the optical densities of the two samples were not identical, the VLT for the boron pyrromethene system was much greater than expected, indicating a more efficient, or narrower, absorption band.

It was observed that the combination of narrowband dyes near 532 nm with the currently used Exciton 1064 nm dye show an interaction causing a drop in optical density at 1064 nm particularly post solarization of the samples. Of the two dyes investigated, the boron pyrromethene dye performed significantly better than the Exciton 527 dye in stabilization of the system leading to a less dramatic drop in OD. The boron pyrromethene dye also was able to provide a significantly higher visible light transmission due to its narrower band and peak absorption closer to 532 nm.

Having thus described several aspects of some embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed:

1. An article, comprising: an optical filter including a substantially optically transparent polymer; and a boron pyrromethene compound associated with the polymer, wherein the optical filter has a quantum yield of fluorescence of about 5% or less upon exposure to electromagnetic radiation between about 300 nm and about 600 nm, wherein the optical filter is included in eyewear, and is selected from the group consisting of a lens, goggle, eyeglasses, and visor.

2. The article according to claim 1, wherein the boron pyrromethene compound is dispersed on or within the polymer formed as a coating on the optical filter.

3. The article according to claim 1, wherein the boron pyrromethene compound is formed as a coating on the optical filter.

4. The article according to claim 1, wherein the boron pyrromethene compound has a maximum absorption peak between about 400 nm and about 800 nm.

5. The article according to claim 4, wherein the boron pyrromethene compound has a maximum absorption peak at about 532 nm.

6. The article according to claim 1, wherein the boron pyrromethene compound comprises an electron-donating group.

7. The article according to claim 1, wherein the boron pyrromethene compound comprises a catechol group.

8. The article according to claim 1, wherein the boron pyrromethene compound has the following structure, wherein:
- each $R^1$-$R^6$ can be the same or different and each is hydrogen, halo, alkyl, alkenyl, alkynyl, cycloalkyl, cycloalkenyl, heterocyclyl, aryl, heteroaryl, OR', N(R')$_2$, or SR', any of which is optionally substituted; and any two of $R^1$-$R^6$ can be joined to form a ring, optionally substituted;
- X is N or CR$^7$, wherein R$^7$ is hydrogen, halo, alkyl, alkenyl, alkynyl, cycloalkyl, cycloalkenyl, heterocyclyl, aryl, heteroaryl, OR', N(R')$_2$, or SR', any of which is optionally substituted;
- $Y^1$ and $Y^2$ can be the same or different and each is halo, OR', N(R')$_2$, or SR', any of which is optionally substituted; or $Y^1$ and $Y^2$ are joined to form a ring, optionally substituted; and
- R' is hydrogen, alkyl, alkenyl, alkynyl, cycloalkyl, cycloalkenyl, heterocyclyl, aryl, or heteroaryl, any of which is optionally substituted.

9. The article according to claim 8, wherein $Y^1$ and $Y^2$ are joined to form a catechol group or a bisnaphthol group, any of which is optionally substituted.

10. The article according to claim 1, wherein the substantially optically transparent polymer is polycarbonate.

11. The article according to claim 1, wherein the boron pyrromethene compound having the following structure, wherein:
- each $R^1$-$R^6$ can be the same or different and each is hydrogen, halo, alkyl, alkenyl, alkynyl, cycloalkyl, cycloalkenyl, heterocyclyl, aryl, heteroaryl, OR', N(R')$_2$, or SR', any of which is optionally substituted; and any two of $R^1$-$R^6$ can be joined to form a ring, optionally substituted;
- R$^7$ is hydrogen, halo, alkyl, alkenyl, alkynyl, cycloalkyl, cycloalkenyl, heterocyclyl, aryl, heteroaryl, OR', N(R')$_2$, or SR', any of which is optionally substituted;
- each $R^8$-$R^{11}$ can be the same or different and each is hydrogen, halo, alkyl, alkenyl, alkynyl, cycloalkyl, cycloalkenyl, heterocyclyl, aryl, heteroaryl, OR', N(R')$_2$, or SR', any of which is optionally substituted; and any two of $R^8$-$R^{11}$ can be joined to form a ring, optionally substituted; and R' is hydrogen, alkyl, alkenyl, alkynyl, cycloalkyl, cycloalkenyl, heterocyclyl, aryl, or heteroaryl, any of which is optionally substituted.

12. The article according to claim 11, wherein the compound has the following structure,

13. The article according to claim 11, wherein the compound has the following structure,

14. The article according to claim 11, wherein the compound has the following structure,

15. The article according to claim 11, wherein the compound has the following structure, 16. The article according to claim 11, wherein the compound has the following structure, 17. The article according to claim 11, wherein the compound has the following structure, 18. An article, comprising: an optical filter including a substantially optically transparent polymer and a boron pyrromethene compound associated with the polymer, wherein, when the article has an optical density of about 4 at an absorbance wavelength, the article has a scotopic luminous transmittance (SLT) from about 10% to about 50%, wherein the optical filter is included in eyewear, and is selected from the group consisting of a lens, goggle, eyeglasses, and visor.

* * * * *